US010945889B2

(12) United States Patent
Locke et al.

(10) Patent No.: US 10,945,889 B2
(45) Date of Patent: Mar. 16, 2021

(54) RELEASABLE MEDICAL DRAPES (71) Applicant: KCI Licensing, Inc., San Antonio, TX (US)

(72) Inventors: Christopher Brian Locke, Bournemouth (GB); Timothy Mark Robinson, Shillingstone (GB); Li Yao, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 655 days.

(21) Appl. No.: 15/600,451

(22) Filed: May 19, 2017

(65) Prior Publication Data

US 2017/0252220 A1 Sep. 7, 2017

Related U.S. Application Data (63) Continuation of application No. 13/715,967, filed on Dec. 14, 2012, now Pat. No. 9,861,532.

(Continued)

(51) Int. Cl.
*A61F 13/00* (2006.01)
*A61F 13/02* (2006.01)

(52) U.S. Cl.
CPC ........ *A61F 13/0216* (2013.01); *A61F 13/025* (2013.01); *A61F 13/0253* (2013.01); *Y10T 156/1056* (2015.01)

(58) Field of Classification Search
CPC ...... A61M 1/0088; A61L 15/58; A61L 31/10; A61L 31/129; A61L 15/26; A61L 15/42; A61L 15/585; A61L 31/047; A61L 31/146; A61L 15/18; A61L 15/24; A61L 15/28; A61L 15/50; A61L 15/60
(Continued)

(56) References Cited

U.S. PATENT DOCUMENTS 1,355,846 A 10/1920 Rannells
1,944,834 A 1/1934 Bennett
(Continued)

FOREIGN PATENT DOCUMENTS

AU 550575 B2 3/1986
AU 745271 B2 3/2002
(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery.
(Continued)

*Primary Examiner* — Kim M Lewis (57) ABSTRACT

A releasable medical drape, and systems and methods having the same, includes at least a liquid-impermeable, vapor-permeable layer, a pressure-sensitive adhesive layer, and a soft-gel layer having a plurality of apertures. The soft-gel layer is configured to be disposed adjacent to a tissue site. A portion of the pressure-sensitive adhesive layer extends through the plurality of apertures in the soft-gel layer to contact the tissue site. The soft-gel layer forms a good seal with the tissue site and the pressure-sensitive adhesive layer extending through the plurality of apertures forms a firm—but releasable—coupling with the tissue site.

6 Claims, 7 Drawing Sheets

Related U.S. Application Data (60) Provisional application No. 61/578,774, filed on Dec. 16, 2011.

(58) Field of Classification Search
USPC .............................. 604/289–292, 313, 540
See application file for complete search history.

(56) References Cited

U.S. PATENT DOCUMENTS

| | | |
|---|---|---|
| 2,547,758 A | 4/1951 | Keeling |
| 2,552,664 A | 5/1951 | Burdine |
| 2,632,443 A | 3/1953 | Lesher |
| 2,682,873 A | 7/1954 | Evans et al. |
| 2,860,081 A | 11/1958 | Eiken |
| 2,910,763 A | 11/1959 | Lauterbach |
| 2,969,057 A | 1/1961 | Simmons |
| 3,066,672 A | 12/1962 | Crosby, Jr. et al. |
| 3,172,808 A | 3/1965 | Baumann et al. |
| 3,183,116 A | 5/1965 | Schaar |
| 3,367,332 A | 2/1968 | Groves |
| 3,376,868 A | 4/1968 | Mondiadis |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,742,952 A | 7/1973 | Magers et al. |
| 3,774,611 A | 11/1973 | Tussey et al. |
| 3,777,016 A | 12/1973 | Gilbert |
| 3,779,243 A | 12/1973 | Tussey et al. |
| 3,826,254 A | 7/1974 | Mellor |
| 3,852,823 A | 12/1974 | Jones |
| 3,903,882 A | 9/1975 | Kugurt |
| 3,967,624 A | 7/1976 | Milnamow |
| 3,983,297 A | 9/1976 | Ono et al. |
| 4,060,081 A | 11/1977 | Yannas et al. |
| 4,080,970 A | 3/1978 | Miller |
| 4,096,853 A | 6/1978 | Weigand |
| 4,139,004 A | 2/1979 | Gonzalez, Jr. |
| 4,141,361 A | 2/1979 | Snyder |
| 4,163,822 A | 8/1979 | Walter |
| 4,165,748 A | 8/1979 | Johnson |
| 4,174,664 A | 11/1979 | Arnott et al. |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,323,069 A | 4/1982 | Ahr et al. |
| 4,333,468 A | 6/1982 | Geist |
| 4,343,848 A | 8/1982 | Leonard, Jr. |
| 4,360,015 A | 11/1982 | Mayer |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,414,970 A | 11/1983 | Berry |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,529,402 A | 7/1985 | Weilbacher et al. |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,600,146 A | 7/1986 | Ohno |
| 4,605,399 A | 8/1986 | Weston et al. |
| 4,608,041 A | 8/1986 | Nielsen |
| 4,617,021 A | 10/1986 | Leuprecht |
| 4,640,688 A | 2/1987 | Hauser |
| 4,655,754 A | 4/1987 | Richmond et al. |
| 4,664,652 A | 5/1987 | Weilbacher |
| 4,664,662 A | 5/1987 | Webster |
| 4,710,165 A | 12/1987 | McNeil et al. |
| 4,715,857 A | 12/1987 | Juhasz et al. |
| 4,733,659 A | 3/1988 | Edenbaum et al. |
| 4,743,232 A | 5/1988 | Kruger |
| 4,753,230 A | 6/1988 | Carus et al. |
| 4,753,232 A | 6/1988 | Ward |
| 4,758,220 A | 7/1988 | Sundblom et al. |
| 4,787,888 A | 11/1988 | Fox |
| 4,826,494 A | 5/1989 | Richmond et al. |
| 4,832,008 A | 5/1989 | Gilman |
| 4,838,883 A | 6/1989 | Matsuura |
| 4,840,187 A | 6/1989 | Brazier |
| 4,848,364 A | 7/1989 | Bosman |
| 4,863,449 A | 9/1989 | Therriault et al. |
| 4,871,611 A | 10/1989 | LeBel |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,930,997 A | 6/1990 | Bennett |
| 4,941,882 A | 7/1990 | Ward et al. |
| 4,953,565 A | 9/1990 | Tachibana et al. |
| 4,961,493 A | 10/1990 | Kaihatsu |
| 4,969,880 A | 11/1990 | Zamierowski |
| 4,981,474 A | 1/1991 | Bopp et al. |
| 4,985,019 A | 1/1991 | Michelson |
| 4,995,382 A | 2/1991 | Lang et al. |
| 4,996,128 A | 2/1991 | Aldecoa et al. |
| 5,010,883 A | 4/1991 | Rawlings et al. |
| 5,018,515 A | 5/1991 | Gilman |
| 5,025,783 A | 6/1991 | Lamb |
| 5,028,597 A | 7/1991 | Kodama et al. |
| 5,037,397 A | 8/1991 | Kalt et al. |
| 5,086,170 A | 2/1992 | Luheshi et al. |
| 5,092,323 A * | 3/1992 | Riedel ............... A61F 13/023 128/888 |
| 5,092,858 A | 3/1992 | Benson et al. |
| 5,100,396 A | 3/1992 | Zamierowski |
| 5,112,323 A | 5/1992 | Winkler et al. |
| 5,127,601 A | 7/1992 | Schroeder |
| 5,134,994 A | 8/1992 | Say |
| 5,149,331 A | 9/1992 | Ferdman et al. |
| 5,151,314 A | 9/1992 | Brown |
| 5,152,757 A | 10/1992 | Eriksson |
| 5,167,613 A | 12/1992 | Karami et al. |
| 5,176,663 A | 1/1993 | Svedman et al. |
| 5,180,375 A | 1/1993 | Feibus |
| 5,215,522 A | 6/1993 | Page et al. |
| 5,232,453 A | 8/1993 | Plass et al. |
| 5,244,457 A | 9/1993 | Karami et al. |
| 5,246,775 A | 9/1993 | Loscuito |
| 5,261,893 A | 11/1993 | Zamierowski |
| 5,266,372 A | 11/1993 | Arakawa et al. |
| 5,270,358 A | 12/1993 | Asmus |
| 5,278,100 A | 1/1994 | Doan et al. |
| 5,279,550 A | 1/1994 | Habib et al. |
| 5,298,015 A | 3/1994 | Komatsuzaki et al. |
| 5,342,329 A | 8/1994 | Croquevielle |
| 5,342,376 A | 8/1994 | Ruff |
| 5,344,415 A | 9/1994 | DeBusk et al. |
| 5,356,386 A | 10/1994 | Goldberg et al. |
| 5,358,494 A | 10/1994 | Svedman |
| 5,384,174 A | 1/1995 | Ward et al. |
| 5,387,207 A | 2/1995 | Dyer et al. |
| 5,419,769 A | 5/1995 | Devlin et al. |
| 5,423,778 A | 6/1995 | Eriksson et al. |
| 5,429,590 A | 7/1995 | Saito et al. |
| 5,437,622 A | 8/1995 | Carion |
| 5,437,651 A | 8/1995 | Todd et al. |
| 5,445,604 A | 8/1995 | Lang |
| 5,447,492 A | 9/1995 | Cartmell et al. |
| 5,458,938 A | 10/1995 | Nygard et al. |
| 5,501,212 A | 3/1996 | Psaros |

(56) References Cited

U.S. PATENT DOCUMENTS

| | | |
|---|---|---|
| 5,522,808 A | 6/1996 | Skalla |
| 5,527,293 A | 6/1996 | Zamierowski |
| 5,549,584 A | 8/1996 | Gross |
| 5,549,585 A | 8/1996 | Maher et al. |
| 5,556,375 A | 9/1996 | Ewall |
| 5,585,178 A | 12/1996 | Calhoun et al. |
| 5,599,292 A | 2/1997 | Yoon |
| 5,607,388 A | 3/1997 | Ewall |
| 5,611,373 A | 3/1997 | Ashcraft |
| 5,634,893 A | 6/1997 | Rishton |
| 5,636,643 A | 6/1997 | Argenta et al. |
| 5,641,506 A | 6/1997 | Talke et al. |
| 5,645,081 A | 7/1997 | Argenta et al. |
| 5,653,224 A | 8/1997 | Johnson |
| 5,678,564 A | 10/1997 | Lawrence et al. |
| 5,710,233 A | 1/1998 | Meckel et al. |
| 5,714,225 A | 2/1998 | Hansen et al. |
| 5,736,470 A | 4/1998 | Schneberger et al. |
| 5,759,570 A | 6/1998 | Arnold |
| 5,776,119 A | 7/1998 | Bilbo et al. |
| 5,807,295 A | 9/1998 | Hutcheon et al. |
| 5,830,201 A | 11/1998 | George et al. |
| 5,878,971 A | 3/1999 | Minnema |
| 5,902,439 A | 5/1999 | Pike et al. |
| 5,919,476 A | 7/1999 | Fischer et al. |
| 5,941,863 A | 8/1999 | Guidotti et al. |
| 5,964,252 A | 10/1999 | Simmons et al. |
| 5,981,822 A | 11/1999 | Addison |
| 5,998,561 A | 12/1999 | Jada |
| 6,071,267 A | 6/2000 | Zamierowski |
| 6,083,616 A | 7/2000 | Dressler |
| 6,086,995 A | 7/2000 | Smith |
| 6,135,116 A | 10/2000 | Vogel et al. |
| 6,174,306 B1 | 1/2001 | Fleischmann |
| 6,191,335 B1 | 2/2001 | Robinson |
| 6,201,164 B1 * | 3/2001 | Wulff ............ A61K 9/0014 602/41 |
| 6,228,485 B1 | 5/2001 | Leiter |
| 6,238,762 B1 | 5/2001 | Friedland et al. |
| 6,241,747 B1 | 6/2001 | Ruff |
| 6,262,329 B1 | 7/2001 | Brunsveld et al. |
| 6,287,316 B1 | 9/2001 | Agarwal et al. |
| 6,345,623 B1 | 2/2002 | Heaton et al. |
| 6,457,200 B1 | 10/2002 | Tanaka et al. |
| 6,458,109 B1 | 10/2002 | Henley et al. |
| 6,488,643 B1 | 12/2002 | Tumey et al. |
| 6,493,568 B1 | 12/2002 | Bell et al. |
| 6,495,229 B1 | 12/2002 | Carte et al. |
| 6,503,855 B1 | 1/2003 | Menzies et al. |
| 6,548,727 B1 | 4/2003 | Swenson |
| 6,553,998 B2 | 4/2003 | Heaton et al. |
| 6,566,575 B1 | 5/2003 | Stickels et al. |
| 6,566,577 B1 | 5/2003 | Addison et al. |
| 6,626,891 B2 | 9/2003 | Ohmstede |
| 6,627,215 B1 | 9/2003 | Dale et al. |
| 6,648,862 B2 | 11/2003 | Watson |
| 6,680,113 B1 | 1/2004 | Lucast et al. |
| 6,685,681 B2 | 2/2004 | Lockwood et al. |
| 6,693,180 B2 | 2/2004 | Lee et al. |
| 6,695,823 B1 | 2/2004 | Lina et al. |
| 6,752,794 B2 | 6/2004 | Lockwood et al. |
| 6,787,682 B2 | 9/2004 | Gilman |
| 6,814,079 B2 | 11/2004 | Heaton et al. |
| 6,855,135 B2 | 2/2005 | Lockwood et al. |
| 6,856,821 B2 | 2/2005 | Johnson |
| 6,979,324 B2 | 12/2005 | Bybordi et al. |
| 7,070,584 B2 | 7/2006 | Johnson et al. |
| 7,154,017 B2 | 12/2006 | Sigurjonsson et al. |
| 7,402,721 B2 | 7/2008 | Sigurjonsson et al. |
| 7,569,742 B2 | 8/2009 | Haggstrom et al. |
| 7,645,269 B2 | 1/2010 | Zamierowski |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,298,197 B2 | 10/2012 | Eriksson et al. |
| 8,398,614 B2 | 3/2013 | Blott et al. |
| 8,449,509 B2 | 5/2013 | Weston |
| 8,529,532 B2 | 9/2013 | Pinto et al. |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,632,523 B2 | 1/2014 | Eriksson et al. |
| 8,679,081 B2 | 3/2014 | Heagle et al. |
| 8,764,732 B2 | 7/2014 | Hartwell |
| 8,834,451 B2 | 9/2014 | Blott et al. |
| 8,920,830 B2 | 12/2014 | Mathies |
| 8,926,592 B2 | 1/2015 | Blott et al. |
| 9,017,302 B2 | 4/2015 | Vitaris et al. |
| 9,192,444 B2 | 11/2015 | Locke et al. |
| 9,198,801 B2 | 12/2015 | Weston |
| 9,211,365 B2 | 12/2015 | Weston |
| 9,289,542 B2 | 3/2016 | Blott et al. |
| 9,861,532 B2 * | 1/2018 | Locke ............ A61F 13/025 |
| 9,877,873 B2 | 1/2018 | Coulthard et al. |
| 9,956,120 B2 | 5/2018 | Locke |
| 2001/0030304 A1 | 10/2001 | Kohda et al. |
| 2001/0051178 A1 | 12/2001 | Blatchford et al. |
| 2002/0009568 A1 | 1/2002 | Bries et al. |
| 2002/0016346 A1 | 2/2002 | Brandt et al. |
| 2002/0065494 A1 | 5/2002 | Lockwood et al. |
| 2002/0077661 A1 | 6/2002 | Saadat |
| 2002/0090496 A1 | 7/2002 | Kim et al. |
| 2002/0115951 A1 | 8/2002 | Norstrem et al. |
| 2002/0119292 A1 | 8/2002 | Venkatasanthanam et al. |
| 2002/0120185 A1 | 8/2002 | Johnson |
| 2002/0130064 A1 | 9/2002 | Adams et al. |
| 2002/0143286 A1 | 10/2002 | Tumey |
| 2002/0150270 A1 | 10/2002 | Werner |
| 2002/0150720 A1 | 10/2002 | Howard et al. |
| 2002/0161346 A1 | 10/2002 | Lockwood et al. |
| 2002/0164346 A1 | 11/2002 | Nicolette |
| 2002/0183702 A1 | 12/2002 | Henley et al. |
| 2002/0198504 A1 | 12/2002 | Risk et al. |
| 2003/0014022 A1 | 1/2003 | Lockwood et al. |
| 2003/0109855 A1 | 6/2003 | Solem et al. |
| 2003/0158577 A1 | 8/2003 | Ginn et al. |
| 2003/0212357 A1 | 11/2003 | Pace |
| 2003/0225347 A1 | 12/2003 | Argenta et al. |
| 2003/0225355 A1 | 12/2003 | Butler |
| 2004/0002676 A1 | 1/2004 | Siegwart et al. |
| 2004/0030304 A1 | 2/2004 | Hunt et al. |
| 2004/0064132 A1 | 4/2004 | Boehringer et al. |
| 2004/0077984 A1 | 4/2004 | Worthley |
| 2004/0082925 A1 | 4/2004 | Patel |
| 2004/0099268 A1 | 5/2004 | Smith et al. |
| 2004/0118401 A1 | 6/2004 | Smith et al. |
| 2004/0127836 A1 | 7/2004 | Sigurjonsson et al. |
| 2004/0127862 A1 | 7/2004 | Bubb et al. |
| 2004/0133143 A1 | 7/2004 | Burton et al. |
| 2004/0163278 A1 | 8/2004 | Caspers et al. |
| 2004/0186239 A1 | 9/2004 | Qin et al. |
| 2004/0219337 A1 | 11/2004 | Langley et al. |
| 2004/0230179 A1 | 11/2004 | Shehada |
| 2005/0034731 A1 | 2/2005 | Rousseau et al. |
| 2005/0054998 A1 | 3/2005 | Poccia et al. |
| 2005/0059918 A1 | 3/2005 | Sigurjonsson et al. |
| 2005/0065484 A1 | 3/2005 | Watson |
| 2005/0070858 A1 | 3/2005 | Lockwood et al. |
| 2005/0101940 A1 | 5/2005 | Radl et al. |
| 2005/0113732 A1 | 5/2005 | Lawry |
| 2005/0124925 A1 | 6/2005 | Scherpenborg |
| 2005/0131327 A1 | 6/2005 | Lockwood et al. |
| 2005/0137539 A1 | 6/2005 | Biggie et al. |
| 2005/0143694 A1 | 6/2005 | Schmidt et al. |
| 2005/0158442 A1 | 7/2005 | Westermann et al. |
| 2005/0159695 A1 | 7/2005 | Cullen et al. |
| 2005/0161042 A1 | 7/2005 | Fudge et al. |
| 2005/0163978 A1 | 7/2005 | Strobech et al. |
| 2005/0214376 A1 | 9/2005 | Faure et al. |
| 2005/0233072 A1 | 10/2005 | Stephan et al. |
| 2005/0256437 A1 | 11/2005 | Silcock et al. |

(56) References Cited

U.S. PATENT DOCUMENTS

| | | |
|---|---|---|
| 2005/0261642 A1 | 11/2005 | Weston |
| 2005/0261643 A1 | 11/2005 | Bybordi et al. |
| 2005/0277860 A1 | 12/2005 | Jensen |
| 2006/0014030 A1 | 1/2006 | Langen et al. |
| 2006/0020235 A1 | 1/2006 | Siniaguine |
| 2006/0079852 A1 | 4/2006 | Bubb et al. |
| 2006/0083776 A1 | 4/2006 | Bott et al. |
| 2006/0154546 A1 | 7/2006 | Murphy et al. |
| 2006/0236979 A1 | 10/2006 | Stolarz et al. |
| 2006/0241542 A1 | 10/2006 | Gudnason et al. |
| 2006/0271020 A1 | 11/2006 | Huang et al. |
| 2007/0027414 A1 | 2/2007 | Hoffman et al. |
| 2007/0028526 A1 | 2/2007 | Woo et al. |
| 2007/0078366 A1 | 4/2007 | Haggstrom et al. |
| 2007/0161937 A1 | 7/2007 | Aali |
| 2007/0185426 A1 | 8/2007 | Ambrosio et al. |
| 2007/0190281 A1 | 8/2007 | Hooft |
| 2007/0225663 A1 | 9/2007 | Watt et al. |
| 2007/0265585 A1 | 11/2007 | Joshi et al. |
| 2007/0265586 A1 | 11/2007 | Joshi et al. |
| 2007/0283962 A1 | 12/2007 | Doshi et al. |
| 2008/0009812 A1 | 1/2008 | Riesinger |
| 2008/0027366 A1 | 1/2008 | Da Silva Macedo |
| 2008/0090085 A1 | 4/2008 | Kawate et al. |
| 2008/0119802 A1 | 5/2008 | Riesinger |
| 2008/0138591 A1 | 6/2008 | Graham et al. |
| 2008/0149104 A1* | 6/2008 | Eifler ................ A61M 16/06 128/206.24 |
| 2008/0173389 A1 | 7/2008 | Mehta et al. |
| 2008/0195017 A1 | 8/2008 | Robinson et al. |
| 2008/0225663 A1 | 9/2008 | Smith et al. |
| 2008/0243044 A1 | 10/2008 | Hunt et al. |
| 2008/0269657 A1 | 10/2008 | Brenneman et al. |
| 2008/0271804 A1 | 11/2008 | Biggie et al. |
| 2009/0025724 A1 | 1/2009 | Herron, Jr. |
| 2009/0088719 A1 | 4/2009 | Driskell |
| 2009/0093779 A1 | 4/2009 | Riesinger |
| 2009/0124988 A1 | 5/2009 | Coulthard |
| 2009/0177172 A1 | 7/2009 | Wilkes |
| 2009/0216168 A1 | 8/2009 | Eckstein |
| 2009/0216170 A1 | 8/2009 | Robinson et al. |
| 2009/0216204 A1 | 8/2009 | Bhavaraju et al. |
| 2009/0227969 A1 | 9/2009 | Jaeb et al. |
| 2009/0234306 A1 | 9/2009 | Vitaris |
| 2009/0234307 A1 | 9/2009 | Vitaris |
| 2009/0264807 A1 | 10/2009 | Haggstrom et al. |
| 2009/0292264 A1 | 11/2009 | Hudspeth et al. |
| 2009/0312662 A1 | 12/2009 | Colman et al. |
| 2009/0326487 A1 | 12/2009 | Vitaris |
| 2009/0326488 A1 | 12/2009 | Budig et al. |
| 2010/0028390 A1 | 2/2010 | Cleary et al. |
| 2010/0030170 A1 | 2/2010 | Keller et al. |
| 2010/0063467 A1 | 3/2010 | Addison et al. |
| 2010/0106106 A1 | 4/2010 | Heaton et al. |
| 2010/0106118 A1 | 4/2010 | Heaton et al. |
| 2010/0125259 A1 | 5/2010 | Olson |
| 2010/0159192 A1* | 6/2010 | Cotton .................. A61L 15/42 428/137 |
| 2010/0168633 A1 | 7/2010 | Bougherara et al. |
| 2010/0168635 A1 | 7/2010 | Freiding et al. |
| 2010/0185163 A1 | 7/2010 | Heagle |
| 2010/0212768 A1 | 8/2010 | Resendes |
| 2010/0226824 A1 | 9/2010 | Ophir et al. |
| 2010/0262090 A1 | 10/2010 | Riesinger |
| 2010/0267302 A1 | 10/2010 | Kantner et al. |
| 2010/0268144 A1 | 10/2010 | Lu et al. |
| 2010/0286582 A1 | 11/2010 | Simpson et al. |
| 2010/0305490 A1 | 12/2010 | Coulthard et al. |
| 2010/0305524 A1 | 12/2010 | Vess et al. |
| 2010/0318072 A1 | 12/2010 | Johnston et al. |
| 2010/0324516 A1 | 12/2010 | Braga et al. |
| 2011/0046585 A1 | 2/2011 | Weston |
| 2011/0054423 A1 | 3/2011 | Blott et al. |
| 2011/0118683 A1 | 5/2011 | Weston |
| 2011/0137271 A1 | 6/2011 | Andresen et al. |
| 2011/0160686 A1 | 6/2011 | Ueda et al. |
| 2011/0171480 A1 | 7/2011 | Mori et al. |
| 2011/0172617 A1 | 7/2011 | Riesinger |
| 2011/0201984 A1 | 8/2011 | Dubrow et al. |
| 2011/0224631 A1 | 9/2011 | Simmons et al. |
| 2011/0229688 A1 | 9/2011 | Cotton |
| 2011/0244010 A1 | 10/2011 | Doshi |
| 2011/0257612 A1 | 10/2011 | Locke et al. |
| 2011/0257617 A1 | 10/2011 | Franklin |
| 2011/0281084 A1 | 11/2011 | Ashwell |
| 2011/0282309 A1 | 11/2011 | Adze et al. |
| 2012/0016322 A1 | 1/2012 | Coulthard et al. |
| 2012/0019031 A1 | 1/2012 | Bessert |
| 2012/0036733 A1 | 2/2012 | Dehn |
| 2012/0040131 A1 | 2/2012 | Speer |
| 2012/0059339 A1 | 3/2012 | Gundersen |
| 2012/0095380 A1 | 4/2012 | Gergely et al. |
| 2012/0109034 A1 | 5/2012 | Locke et al. |
| 2012/0123359 A1 | 5/2012 | Reed |
| 2012/0143157 A1 | 6/2012 | Riesinger |
| 2012/0237722 A1 | 9/2012 | Seyler et al. |
| 2012/0258271 A1 | 10/2012 | Maughan |
| 2012/0310186 A1 | 12/2012 | Moghe et al. |
| 2013/0030394 A1 | 1/2013 | Locke et al. |
| 2013/0053746 A1 | 2/2013 | Roland et al. |
| 2013/0066285 A1 | 3/2013 | Locke et al. |
| 2013/0096518 A1 | 4/2013 | Hall et al. |
| 2013/0098360 A1 | 4/2013 | Hurmez et al. |
| 2013/0116661 A1 | 5/2013 | Coward et al. |
| 2013/0150763 A1 | 6/2013 | Mirzaei et al. |
| 2013/0152945 A1 | 6/2013 | Locke et al. |
| 2013/0165887 A1 | 6/2013 | Mitchell et al. |
| 2013/0172843 A1 | 7/2013 | Kurata |
| 2013/0189339 A1* | 7/2013 | Vachon ................ A61K 31/167 424/404 |
| 2013/0261585 A1 | 10/2013 | Lee |
| 2013/0304007 A1 | 11/2013 | Toth |
| 2013/0330486 A1 | 12/2013 | Shields |
| 2014/0039423 A1 | 2/2014 | Riesinger |
| 2014/0039424 A1 | 2/2014 | Locke |
| 2014/0058309 A1 | 2/2014 | Addison et al. |
| 2014/0107561 A1 | 4/2014 | Dorian et al. |
| 2014/0107562 A1 | 4/2014 | Dorian et al. |
| 2014/0141197 A1 | 5/2014 | Hill et al. |
| 2014/0155849 A1 | 6/2014 | Heaton et al. |
| 2014/0163491 A1 | 6/2014 | Schuessler et al. |
| 2014/0171851 A1 | 6/2014 | Addison |
| 2014/0178564 A1 | 6/2014 | Patel |
| 2014/0309574 A1 | 10/2014 | Cotton |
| 2014/0336557 A1 | 11/2014 | Durdag et al. |
| 2014/0350494 A1 | 11/2014 | Hartwell et al. |
| 2014/0352073 A1 | 12/2014 | Goenka |
| 2015/0030848 A1 | 1/2015 | Goubard |
| 2015/0045752 A1 | 2/2015 | Grillitsch et al. |
| 2015/0057625 A1 | 2/2015 | Coulthard |
| 2015/0080788 A1 | 3/2015 | Blott et al. |
| 2015/0080815 A1 | 3/2015 | Chakravarthy et al. |
| 2015/0119830 A1 | 4/2015 | Luckemeyer et al. |
| 2015/0119833 A1 | 4/2015 | Coulthard et al. |
| 2015/0119834 A1 | 4/2015 | Locke et al. |
| 2015/0141941 A1 | 5/2015 | Allen et al. |
| 2015/0190286 A1 | 7/2015 | Allen et al. |
| 2015/0290041 A1 | 10/2015 | Richard |
| 2016/0000610 A1 | 1/2016 | Riesinger |
| 2016/0067107 A1 | 3/2016 | Cotton |
| 2016/0144084 A1 | 5/2016 | Collinson et al. |

FOREIGN PATENT DOCUMENTS

| | | |
|---|---|---|
| AU | 755496 B2 | 12/2002 |
| AU | 2009200608 A1 | 10/2009 |
| CA | 2005436 A1 | 6/1990 |
| CN | 87101823 A | 8/1988 |
| DE | 26 40 413 A1 | 3/1978 |
| DE | 43 06 478 A1 | 9/1994 |
| DE | 29 504 378 U1 | 9/1995 |
| DE | 202004018245 U1 | 7/2005 |
| DE | 202014100383 U1 | 2/2015 |
| EP | 0097517 A1 | 1/1984 |

(56) References Cited

FOREIGN PATENT DOCUMENTS

| | | |
|---|---|---|
| EP | 01001481 | 2/1984 |
| EP | 0117632 A2 | 9/1984 |
| EP | 0161865 A2 | 11/1985 |
| EP | 0251810 A2 | 1/1988 |
| EP | 0275353 A2 | 7/1988 |
| EP | 0358302 A2 | 3/1990 |
| EP | 0538917 A1 | 4/1993 |
| EP | 0630629 A1 | 12/1994 |
| EP | 0659390 A2 | 6/1995 |
| EP | 0633758 B1 | 10/1996 |
| EP | 1002846 A1 | 5/2000 |
| EP | 1018967 A1 | 7/2000 |
| EP | 2578193 A1 | 4/2013 |
| GB | 692578 A | 6/1953 |
| GB | 1386800 A | 3/1975 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| GB | 2377939 A | 1/2003 |
| GB | 2392836 A | 3/2004 |
| GB | 2393655 A | 4/2004 |
| GB | 2425487 A | 11/2006 |
| GB | 2452720 A | 3/2009 |
| GB | 2496310 A | 5/2013 |
| JP | 1961003393 | 2/1961 |
| JP | S62139523 U | 9/1987 |
| JP | S62-275456 A | 11/1987 |
| JP | 2005205120 A | 8/2005 |
| JP | 2007254515 A | 10/2007 |
| JP | 2008080137 A | 4/2008 |
| JP | 4129536 B2 | 8/2008 |
| JP | 2012050274 A | 3/2012 |
| SG | 71559 | 4/2002 |
| WO | 80/02182 A1 | 10/1980 |
| WO | 87/04626 A1 | 8/1987 |
| WO | 8707164 A1 | 12/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 9622753 A1 | 8/1996 |
| WO | 97/18007 A1 | 5/1997 |
| WO | 99/13793 A1 | 3/1999 |
| WO | 99/65542 A1 | 12/1999 |
| WO | 01/36188 A1 | 5/2001 |
| WO | 01/60296 A1 | 8/2001 |
| WO | 0168021 A1 | 9/2001 |
| WO | 0185248 A1 | 11/2001 |
| WO | 0190465 A2 | 11/2001 |
| WO | 0243743 A1 | 6/2002 |
| WO | 02062403 A1 | 8/2002 |
| WO | 03-018098 A2 | 3/2003 |
| WO | 03045294 A1 | 6/2003 |
| WO | 03045492 A1 | 6/2003 |
| WO | 03053484 A1 | 7/2003 |
| WO | 2004024197 A1 | 3/2004 |
| WO | 2004037334 A1 | 5/2004 |
| WO | 2004112852 A1 | 12/2004 |
| WO | 2005002483 A2 | 1/2005 |
| WO | 2005062896 A2 | 7/2005 |
| WO | 2005105176 A1 | 11/2005 |
| WO | 2005123170 A1 | 12/2005 |
| WO | 2007022097 A2 | 2/2007 |
| WO | 2007030601 A2 | 3/2007 |
| WO | 2007070269 A1 | 6/2007 |
| WO | 2007085396 A1 | 8/2007 |
| WO | 2007087811 A1 | 8/2007 |
| WO | 2007113597 A2 | 10/2007 |
| WO | 2007133618 A2 | 11/2007 |
| WO | 2008026117 A1 | 3/2008 |
| WO | 2008041926 A1 | 4/2008 |
| WO | 2008048527 A2 | 4/2008 |
| WO | 2008054312 A1 | 5/2008 |
| WO | 2008/082444 A2 | 7/2008 |
| WO | 2008/100440 A1 | 8/2008 |
| WO | 2008104609 A1 | 9/2008 |
| WO | 2008/131895 A1 | 11/2008 |
| WO | 2009/002260 A1 | 12/2008 |
| WO | 2008149107 A1 | 12/2008 |
| WO | 2009066105 A1 | 5/2009 |
| WO | 2009066106 A1 | 5/2009 |
| WO | 2009081134 A1 | 7/2009 |
| WO | 2009089016 A1 | 7/2009 |
| WO | 2009/124100 A1 | 10/2009 |
| WO | 2009126103 A1 | 10/2009 |
| WO | 2010011148 A1 | 1/2010 |
| WO | 2010016791 A1 | 2/2010 |
| WO | 2010032728 A1 | 3/2010 |
| WO | 2010/056977 A2 | 5/2010 |
| WO | 2010129299 A2 | 11/2010 |
| WO | 2011008497 A2 | 1/2011 |
| WO | 2011/049562 A1 | 4/2011 |
| WO | 2011043786 A1 | 4/2011 |
| WO | 2011115908 A1 | 9/2011 |
| WO | 2011121127 A1 | 10/2011 |
| WO | 2011130570 A1 | 10/2011 |
| WO | 2011162862 A1 | 12/2011 |
| WO | 2012/112204 A1 | 8/2012 |
| WO | 2012104584 A1 | 8/2012 |
| WO | 2012140378 A1 | 10/2012 |
| WO | 2012143665 A1 | 10/2012 |
| WO | 2013009239 A1 | 1/2013 |
| WO | 2013066426 A2 | 5/2013 |
| WO | 2013090810 A1 | 6/2013 |
| WO | 2014022400 A1 | 2/2014 |
| WO | 2014039557 A1 | 3/2014 |
| WO | 2014078518 A1 | 5/2014 |
| WO | 2014/113253 A1 | 7/2014 |
| WO | 2014140608 A1 | 9/2014 |
| WO | 2014143488 A1 | 9/2014 |
| WO | 2015/065615 A1 | 5/2015 |
| WO | 2015130471 A1 | 9/2015 |
| WO | 2017048866 A1 | 3/2017 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

(56) References Cited

OTHER PUBLICATIONS

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E, M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.
Office Action for related U.S. Appl. No. 14/965,675, dated Dec. 12, 2018.
Office Action for related U.S. Appl. No. 14/619,714, dated Dec. 3, 2018.
Office Action for related U.S. Appl. No. 14/630,290, dated Jan. 11, 2019.
Office Action for related U.S. Appl. No. 15/265,718, dated Feb. 7, 2019.
Extended European Search Report for related application 18193559.4, dated Dec. 17, 2018.
Office Action for related U.S. Appl. No. 14/080,348, dated Apr. 12, 2019.
Japanese Notice of Rejection for related application 2016-570333, dated Feb. 26, 2019.
Office Action for related U.S. Appl. No. 15/410,991, dated May 2, 2019.
International Search Report and Written Opinion for PCT/US2012/069893 dated Apr. 8, 2013.
International Search Report and Written Opinion for PCT/GB2008/003075 dated Mar. 11, 2010.
International Search Report and Written Opinion for PCT/GB2008/004216 dated Jul. 2, 2009.
International Search Report and Written Opinion for PCT/GB2012/000099 dated May 2, 2012.
EP Examination Report for corresponding application 12705381.7, dated May 22, 2014.
International Search Report and Written Opinion for PCT/US2013/070070 dated Jan. 29, 2014.
International Search Report and Written Opinion for PCT/US2014/016320 dated Apr. 15, 2014.
International Search Report and Written Opinion for PCT/US2014/056566 dated Dec. 5, 2014.
International Search Report and Written Opinion for PCT/US2014/056508 dated Dec. 9, 2014.
International Search Report and Written Opinion for PCT/US2014/056524 dated Dec. 11, 2014.
International Search Report and Written Opinion for PCT/US2014/056594 dated Dec. 2, 2014.
International Search Report and Written opinion date dated Dec. 15, 2009; PCT Internation Application No. PCT/US2009/036222.
Response filed Oct. 20, 2011 for U.S. Appl. No. 12/398,904.
Interview Summary dated Oct. 27, 2011 for U.S. Appl. No. 12/398,904.
Non-Final Office Action dated Jul. 20, 2011 for U.S. Appl. No. 12/398,904.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medican Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in All-Union Conference on Wounds and Wound Infections: Presentation Abstracts, (56) References Cited

OTHER PUBLICATIONS edited by B.M. Kostyuchenok et al. (Moscow, U.S.S.R. Oct. 28-29, 1986) pp. 91-92 ("Bagautdinov II").
NDP 1000 Negative Pressure Wound Terapy System, Kalypto Medical, pp. 1-4.
Examination report for AU2009221772 dated Apr. 4, 2013.
Response filed Oct. 21, 2011 for U.S. Appl. No. 12/398,891.
Interview Summary dated Oct. 27, 2011 for U.S. Appl. No. 12/398,891.
Restriction Requirement dated Jun. 13, 2011 for U.S. Appl. No. 12/398,891.
Response filed Jun. 24, 2011 for U.S. Appl. No. 12/398,891.
Non-Final Office Action dated Jul. 21, 2011 for U.S. Appl. No. 12/398,891.
International Search Report and Written Opinion dated Oct. 19, 2010; PCT International Application No. PCT/US2009/036217.
NPD 1000 Negative Pressure Would Therapy System, Kalypto Medical, pp. 1-4.
Non-Final Rejection for U.S. Appl. No. 12/398,904 dated Mar. 14, 2012.
Response to Non-Final Rejection for U.S. Appl. No. 12/398,904, filed Jun. 4, 2012.
International Search Report and Written Opinion for PCT/US2014/061251 dated May 8, 2015.
International Search Report and Written Opinion for PCT/IB2013/060862 dated Jun. 26, 2014.
International Search Report and Written Opinion for PCT/US2015/015493 dated May 4, 2015.
European Search Report for corresponding Application No. 15194949.2.
European Search Report for corresponding EPSN 15157408.4 published on Sep. 30, 2015.
International Search Report and Written Opinion for PCT/US2015/034289 dated Aug. 21, 2015.
International Search Report and Written Opinion for PCT/US2015/065135 dated Apr. 4, 2016.
International Search Report and Written Opinion for PCT/GB2012/050822 dated Aug. 8, 2012.
International Search Report and Written Opinion for PCT/US2015/029037 dated Sep. 4, 2015.
International Search Report and Written Opinion date dated Jun. 1, 2011 for PCT International Application No. PCT/US2011/028344.
European Search Report for EP 11714148.1, dated May 2, 2014.
European Search Report for corresponding Application No. 15192606.0 dated Feb. 24, 2016.
International Search Report and Written Opinion for corresponding PCT/US2014/048081 dated Nov. 14, 2014.
International Search Report and Written Opinion for corresponding PCT/US2014/010704 dated Mar. 25, 2014.
European Examination Report dated Jun. 29, 2016, corresponding to EP Application No. 16173614.5.
International Search Report and Written Opinion for corresponding PCT application PCT/US2016/051768 dated Dec. 15, 2016.
European Search Report for corresponding EP Application 171572787 dated Jun. 6, 2017.
International Search Report and Written Opinion for corresponding application PCT/US2016/031397, dated Aug. 8, 2016.
European Search Report for corresponding application 17167872.5, dated Aug. 14, 2017.
Office Action for related U.S. Appl. No. 15/314,426, dated Aug. 29, 2019.
Office Action for related U.S. Appl. No. 14/965,675, dated Aug. 9, 2018.
Office Action for related U.S. Appl. No. 15/307,472, dated Oct. 18, 2018.
Extended European Search Report for related application 17177013.4, dated Mar. 19, 2018.
Extended European Search Report for related application 16793298.7, dated Mar. 27, 2018.
M. Waring et al., "Cell attachment to adhesive dressing: qualitative and quantitative analysis", Wounds, UK, (2008), vol. 4, No. 3, pp. 35-47.
R. White, "Evidence for atraumatic soft silicone wound dressing use". Wound, UK (2005), vol. 3, pp. 104-108, Mepilex Border docs, (2001).
European Search Report for corresponding application 17183683.6, dated Sep. 18, 2017.
European Search Report for corresponding application 17164033.7, dated Oct. 13, 2017.
Extended European Search Report for corresponding application 17191970.7, dated Oct. 26, 2017.
Japanese office action for corresponding application 2015-547246, dated Sep. 5, 2017.
Office Action for related U.S. Appl. No. 13/982,650, dated Dec. 14, 2017.
Australian Office Action for related application 2013344686, dated Nov. 28, 2017.
Office Action for related U.S. Appl. No. 14/517,521, dated Dec. 12, 2017.
Office Action for related U.S. Appl. No. 14/490,898, dated Jan. 4, 2018.
International Search Report and Written Opinion for related appplication PCT/US2017/058209, dated Jan. 10, 2018.
Office Action for related U.S. Appl. No. 14/965,675, dated Jan. 31, 2018.
International Search Report and Written Opinion for related application PCT/US2016/047351, dated Nov. 2, 2016.
Australian Office Action for related application 2018278874, dated Feb. 12, 2020.
Office Action for related U.S. Appl. No. 14/630,290, dated Apr. 30, 2020.
Office Action for related U.S. Appl. No. 15/793,044, dated May 13, 2020.
EP Informal Search Report for related application 19186600.3, dated May 11, 2020.
Office Action for related U.S. Appl. No. 15/884,198, dated May 19, 2020.
Office Action for related U.S. Appl. No. 16/007,060, dated Aug. 18, 2020.
Office Action for related U.S. Appl. No. 15/937,485, dated Aug. 4, 2020.
Office Action for related U.S. Appl. No. 15/793,044, dated Sep. 24, 2020
Extended European Search Report for related application 20185730.7, dated Oct. 9, 2020.
Advisory Action for related U.S. Appl. No. 15/793,044, dated Dec. 9, 2020.

\* cited by examiner

RELEASABLE MEDICAL DRAPES

RELATED APPLICATIONS

This application is a continuation of U.S. patent application Ser. No. 13/715,967, filed Dec. 14, 2012, issued as U.S. Pat. No. 9,861,532, which claims priority to U.S. Provisional Patent Application No. 61/576,774, filed Dec. 16, 2011, entitled "Releasable Medical Drapes," the disclosure of which is hereby incorporated by reference in its entirety.

TECHNICAL FIELD

The present disclosure relates generally to dressings for adhering to a patient, and more particularly, but not by way of limitation, to releasable medical drapes, systems, and methods.

BACKGROUND

Clinical studies and practice have shown that providing reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, which may include faster healing and increased formulation of granulation tissue.

In applying reduced-pressure therapy, typically a foam pad or other manifold is placed proximate to the wound and covered with a drape to form a sealed space, and reduced pressure is applied to the sealed space. If the drape leaks, additional energy may be required to overcome the leak and maintain a therapeutic level of reduced pressure.

SUMMARY

According to an illustrative, non-limiting embodiment, a releasable medical drape for providing a seal over a tissue site on a patient includes a liquid-impermeable, vapor-permeable layer having a first side and a second, patient-facing side and a pressure-sensitive adhesive layer having a first side and a second, patient-facing side. The first side of the pressure-sensitive adhesive layer is coupled to the second, patient-facing side of the liquid-impermeable, vapor-permeable layer. The releasable medical drape also includes a soft-gel layer formed with a plurality of apertures and having a first side and a second, patient-facing side. The first side of the soft-gel layer is coupled to the second, patient-facing side of the pressure-sensitive adhesive layer. The pressure-sensitive adhesive layer is configured to extend at least partially through the plurality of apertures in the soft-gel layer when hand pressure is applied to the first side of the liquid-impermeable, vapor-permeable layer.

According to another illustrative embodiment, a system for treating a tissue site on a patient with reduced pressure includes a manifold disposed proximate to the tissue site for distributing reduced pressure, a releasable medical drape disposed over the manifold and a portion of intact skin to form a sealed space that contains the manifold, and a reduced-pressure source fluidly coupled to the sealed space. The releasable medical drape includes a liquid-impermeable, vapor-permeable layer having a first side and a second, patient-facing side and a pressure-sensitive adhesive layer having a first side and a second, patient-facing side. The first side of the pressure-sensitive adhesive layer is coupled to the second, patient-facing side of the liquid-impermeable, vapor-permeable layer. The releasable medical drape also includes a soft-gel layer formed with a plurality of apertures and having a first side and a second, patient-facing side. The first side of the soft-gel layer is coupled to the second, patient-facing side of the pressure-sensitive adhesive layer. The pressure-sensitive adhesive layer is configured to extend at least partially through the plurality of apertures in the soft-gel layer when hand pressure is applied to the first side of the liquid-impermeable, vapor-permeable layer.

According to another illustrative embodiment, a method of treating a tissue site on a patient includes: disposing a manifold proximate to the tissue for distributing reduced pressure and covering the manifold and a portion of intact skin with a releasable medical drape. The releasable medical drape includes a liquid-impermeable, vapor-permeable layer having a first side and a second, patient-facing side, and a pressure-sensitive adhesive layer having a first side and a second, patient-facing side. The first side of the pressure-sensitive adhesive layer is coupled to the second, patient-facing side of the liquid-impermeable, vapor-permeable layer. The releasable medical drape also includes a soft-gel layer formed with a plurality of apertures and having a first side and a second, patient-facing side. The first side of the soft-gel layer is coupled to the second, patient-facing side of the pressure-sensitive adhesive layer. The pressure-sensitive adhesive layer is configured to extend at least partially through the plurality of apertures in the soft-gel layer when hand pressure is applied to the first side of the liquid-impermeable, vapor-permeable layer. The method further includes rubbing the first side of the liquid-impermeable, vapor-permeable layer by hand to cause at least a portion of the pressure-sensitive adhesive layer to extend into the plurality of apertures and into contact with the intact skin. The method also delivers reduced pressure to the manifold.

According to another illustrative embodiment, a method of manufacturing a releasable medical drape includes providing a soft-gel layer having a first side and a second side, forming a plurality of apertures in the soft-gel layer, and providing a liquid-impermeable, vapor-permeable layer having a first side and a second side. The method further includes providing a pressure-sensitive adhesive layer having a first side and a second side and coupling the first side of the pressure-sensitive adhesive layer to the second side of the liquid-impermeable, vapor-permeable layer. The method also includes coupling the second side of the pressure-sensitive adhesive layer to the first side of the soft-gel layer. The pressure-sensitive adhesive layer is positioned to extend through the plurality of apertures.

According to another illustrative embodiment, a releasable medical drape for forming a sealed space adjacent a tissue site on a patient includes a polyurethane outer layer having a thickness between about 15 microns and about 50 microns; a pressure-sensitive adhesive layer adjacent to the polyurethane out layer; and a silicone gel layer having thickness between about 1200 and about 4100 microns formed with a plurality of apertures. A portion of the pressure-sensitive adhesive layer extends through the plurality of apertures to contact the tissue site when the polyurethane outer layer is rubbed by hand.

According to another illustrative embodiment, a releasable medical drape for providing a seal over a tissue site on a patient includes a liquid-impermeable, vapor-permeable layer having a first side and a second, patient-facing side, and a first mesh layer having a first side and a second, patient-facing side. The first side of the first mesh layer is coupled to the second, patient-facing side of the liquid-impermeable, vapor-permeable layer. At least the second, patient-facing side of the first mesh layer is substantially coated with a pressure-sensitive adhesive. The releasable medical drape further includes a second mesh layer having a first side and a second, patient-facing side. The first side of the second mesh layer is coupled to the second, patient-facing side of the first mesh layer. At least the second, patient-facing side of the second mesh layer is substantially coated with a soft-gel. The pressure-sensitive adhesive of the first mesh layer is configured to extend at least partially through void portions of the second mesh layer when hand pressure is applied to the first side of the liquid-impermeable, vapor-permeable layer.

According to another illustrative embodiment, a releasable medical drape for providing a seal adjacent a tissue site on a patient includes a liquid-impermeable, vapor-permeable layer having a first side and a second, patient-facing side, and a first plurality of strands substantially coated with a pressure-sensitive adhesive. The plurality of strands are coupled to the second, patient-facing side of the liquid-impermeable, vapor-permeable layer. The releasable medical drape also includes a second plurality of strands substantially coated with a soft-gel. The second plurality of strands is coupled at least in part to liquid-impermeable, vapor-permeable layer. The pressure-sensitive adhesive of the first plurality of strands is configured to extend at least partially beyond the second plurality of strands to contact the patient when hand pressure is applied to the first side of the liquid-impermeable, vapor-permeable layer.

Other aspects, features, and advantages of the illustrative embodiments will become apparent with reference to the drawings and detailed description that follow.

DETAILED DESCRIPTION OF ILLUSTRATIVE EMBODIMENTS

In the following detailed description of illustrative, non-limiting embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is not to be taken in a limiting sense, and the scope of the illustrative embodiments is defined only by the appended claims.

Figure 1:
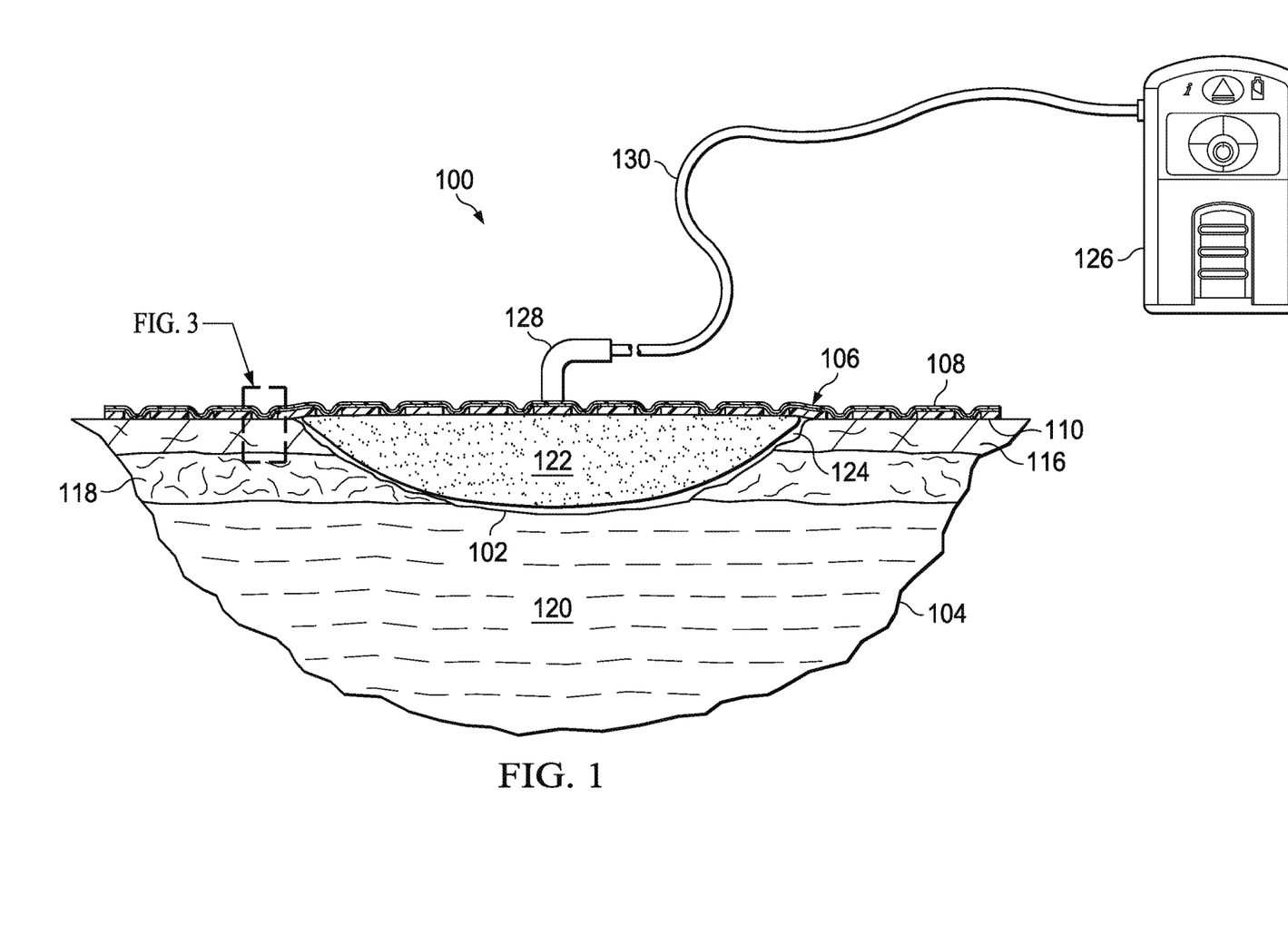
FIG. 1 is a cross-sectional view (with a portion shown in elevation) of an illustrative embodiment of a system for treating a tissue site on a patient with reduced pressure.
Figure 2:
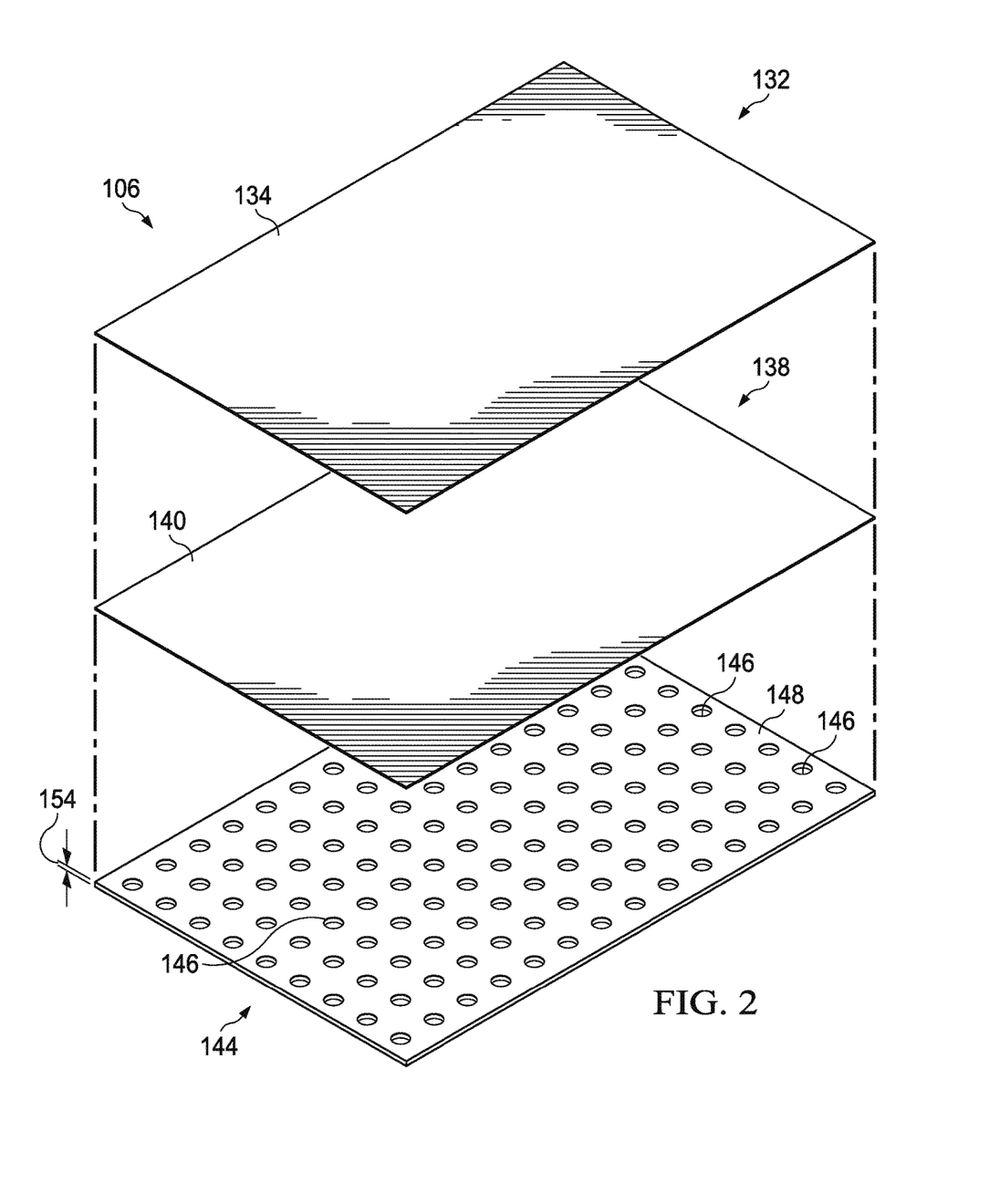
FIG. 2 is an exploded perspective view of an illustrative embodiment of a releasable medical drape.
Figure 3:
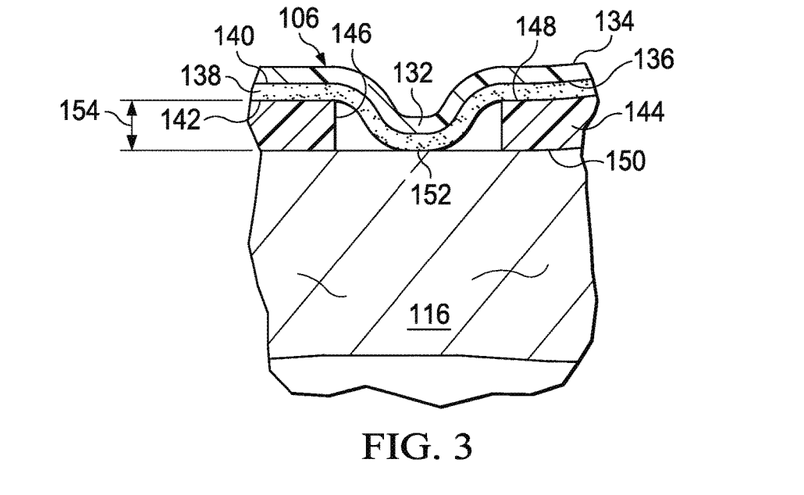
FIG. 3 is a detail in cross section of a portion of the system of FIG. 1.

Referring now to the figures and primarily to FIGS. 1-3, a system 100 for treating a tissue site 102 on a patient 104 with reduced pressure is presented. The system 100 includes a releasable medical drape 106 having a first side 108 and a second, patient-facing side 110. The releasable medical drape 106 provides a seal to the tissue site 102. The seal formed has substantially no leaks. The releasable medical drape 106 allows vapor to egress the releasable medical drape 106, maintains an adequately strong mechanical connection to the intact skin 112, is easy to apply, is easy to remove, and causes minimal pain to the patient during removal. The releasable medical drape 106 is described in more detail below.

The tissue site 102 may be the bodily tissue of any human, animal, or other organism, including bone tissue, adipose tissue, muscle tissue, dermal tissue, vascular tissue, connective tissue, cartilage, tendons, ligaments, or any other tissue. Treatment of the tissue site 102 may include removal of fluids, for example, exudate or ascites. As used throughout this document, "or" does not require mutual exclusivity. In the illustrative example of FIGS. 1-3, the tissue site 102 is a wound on the patient 104. In the illustrated embodiment, the wound extends through epidermis 116, through dermis 118, and into subcutaneous tissue 120.

A manifold 122 is disposed proximate to the tissue site 102. The manifold 122 is a substance or structure that is provided to assist in applying reduced pressure to, delivering fluids to, or removing fluids from the tissue site 102. The manifold 122 includes a plurality of flow channels or pathways that can distribute fluids provided to and removed from the tissue site 102. In one illustrative embodiment, the flow channels or pathways are interconnected to improve distribution of fluids provided to or removed from the tissue site 102. The manifold 122 may comprise one or more of the following: a biocompatible material that is capable of being placed in contact with the tissue site 102 and distributing reduced pressure to the tissue site 102; devices that have structural elements arranged to form flow channels, such as, for example, cellular foam, open-cell foam, porous tissue collections, liquids, gels, and foams that include, or cure to include, flow channels; porous material, such as foam, gauze, felted mat, or any other material suited to a particular biological application; or porous foam that includes a plurality of interconnected cells or pores that act as flow channels, e.g., a polyurethane, open-cell, reticulated foam such as GranuFoam® material manufactured by Kinetic Concepts, Incorporated of San Antonio, Tex.; a bioresorbable material; or a scaffold material. In some situations, the manifold 122 may also be used to distribute fluids such as medications, anti-bacterials, growth factors, and various solutions to the tissue site 102.

The releasable medical drape 106 is disposed over the manifold 122 and at least a portion of the tissue site to form a sealed space 124. The sealed space 124 contains the manifold 122. A reduced-pressure source 126 is fluidly coupled to the sealed space 124. The reduced-pressure source 126 provides reduced pressure. The reduced-pressure source 126 may be any device for supplying a reduced pressure, such as a vacuum pump, wall suction, a micropump, or other source. While the amount and nature of reduced pressure applied to a tissue site will typically vary according to the application, the reduced pressure will typically be between −5 mm Hg (−667 Pa) and −500 mm Hg (−66.7 kPa) and more typically between −75 mm Hg (−9.9 kPa) and −300 mm Hg (−39.9 kPa) and more typically still between 75 mm Hg (−9.9 kPa) and −200 mm Hg (−26.66 kPa).

A reduced-pressure interface 128 may be used to fluidly couple a reduced-pressure delivery conduit 130 to the sealed space 124. The reduced pressure developed by the reduced-pressure source 126 is delivered through the reduced-pressure delivery conduit 130 to the reduced-pressure interface 128. In one illustrative embodiment, the reduced-pressure interface 128 is a T.R.A.C.® Pad or Sensa T.R.A.C.® Pad available from KCI of San Antonio, Tex. The reduced-pressure interface 128 allows the reduced pressure to be delivered to the sealed space 124. The reduced-pressure interface 128 may also be a conduit inserted through the releasable medical drape 106. The reduced pressure may also be generated by a device, e.g., a micro-pump, directly coupled to the releasable medical drape 106.

Referring primarily to FIGS. 2 and 3, the releasable medical drape 106 has three primary layers (going from the outer-most layer to the layer contacting the patient): (1) a liquid-impermeable, vapor-permeable layer 132, (2) a pressure-sensitive adhesive layer 138; and (3) a soft-gel layer 144 having a plurality of apertures 146. The liquid-impermeable, vapor-permeable layer 132 functions as a barrier to liquids and microorganisms. The pressure-sensitive adhesive layer 138 provides a means for coupling the liquid-impermeable, vapor-permeable layer 132 to the soft-gel layer 144. In addition, in operation, a portion of the pressure-sensitive adhesive layer 138 extends through the plurality of apertures 146 to contact the epidermis 116 and thereby provide a contact coupling 152 between the releasable medical drape 106 and the patient 104. The contact coupling is releasable and yet provides sufficient coupling to adhere to the patient 104 during use.

The liquid-impermeable, vapor-permeable layer 132 has a first side 134 and a second, patient-facing side 136. The liquid-impermeable, vapor-permeable layer 132 allows vapor to egress and inhibits liquids from exiting. The liquid-impermeable, vapor-permeable layer 132 is a flexible film that is breathable and typically has a high moisture vapor transfer rate (MVTR), for example, greater than or equal to about 300 g/m$^2$/24 hours. The liquid-impermeable, vapor-permeable layer 132 may be formed from a range of medically approved films ranging in thickness typically from about 15 microns (μm) to about 50 microns (μm), for example, 15, 20, 25, 30, 35, 40, 45, or 50 microns (μm), or any number in the stated range. In alternative embodiments, a low or no vapor transfer drape might be used.

The liquid-impermeable, vapor-permeable layer 132 may comprise numerous materials, such as one or more of the following: hydrophilic polyurethane (PU), cellulosics, hydrophilic polyamides, polyvinyl alcohol, polyvinyl pyrrolidone, hydrophilic acrylics, hydrophilic silicone elastomers, and copolymers of these. As one specific, illustrative, non-limiting embodiment, the liquid-impermeable, vapor-permeable layer 132 may be formed from a breathable cast matt polyurethane film sold by Expopack Advanced Coatings of Wrexham, United Kingdom, under the name INSPIRE 2301. That illustrative film has a MVTR (inverted cup technique) of 14400 g/m$^2$/24 hours and is approximately 30 microns thick.

Adjacent to the liquid-impermeable, vapor-permeable layer 132 is the pressure-sensitive adhesive layer 138. The pressure-sensitive adhesive layer 138 has a first side 140 and a second, patient-facing side 142. The pressure-sensitive adhesive layer 138 may be any medically-acceptable, pressure-sensitive adhesive. For example, the pressure-sensitive adhesive layer 138 may comprise an acrylic adhesive, rubber adhesive, high-tack silicone adhesive, polyurethane, or other substance. In an illustrative example, the pressure-sensitive adhesive layer 138 comprises an acrylic adhesive with coating weight of 15 grams/m$^2$ (gsm) to 70 grams/m$^2$ (gsm). The pressure-sensitive adhesive layer 138 may be a continuous layer of material or may be a layer with apertures (not shown). The apertures may be formed after application of the pressure-sensitive adhesive layer 138 or may be formed by coating the pressure-sensitive adhesive layer 138 in patterns on a carrier layer, e.g., the second, patient-facing side 136 of the liquid-impermeable, vapor-permeable layer 132. The apertures may be sized to help control the resultant tackiness when the pressure-sensitive adhesive layer 138 is forced into apertures 146. The apertures may also be sized to enhance the MVTR of the releasable medical drape 106.

The soft-gel layer 144 has a first side 148 and a second, patient-facing side 150. The soft-gel layer 144 is a soft material that provides a good seal with the tissue site 102. The soft-gel layer 144 may comprise a silicone gel (or soft silicone), hydrocolloid, hydrogel, polyurethane gel, polyolefin gel, hydrogenated styrenic copolymer gels, or foamed gels with compositions as listed, or soft closed cell foams (polyurethanes, polyolefins) coated with an adhesive (e.g., 30 gsm-70 gsm acrylic), polyurethane, polyolefin, or hydrogenated styrenic copolymers. The soft-gel layer 144 has a thickness 154 that is typically in the range of about 500 microns (μm) to about 1000 microns (μm). The soft-gel layer 144 in one embodiment has stiffness between about 5 Shore OO and about 80 Shore OO. The soft-gel layer 144 may be hydrophobic or hydrophilic.

The soft-gel layer 144 is formed with the plurality of apertures 146. The apertures 146 may be numerous shapes, for example, circles, squares, stars, ovals, polygons, slits complex curves, rectilinear shapes, triangles, or other shapes. Each aperture 146 of the plurality of apertures 146 has an effective diameter, which is the diameter of a circular area having the same surface area as the aperture 146. The average effective diameter is typically in the range of about 6 mm to about 50 mm. The plurality of apertures 146 may have a uniform pattern or may be randomly distributed on the soft-gel layer 144.

In the assembled state, the first side 140 of the pressure-sensitive adhesive layer 138 is coupled to the second, patient-facing side 136 of the liquid-impermeable, vapor-permeable layer 132. The first side 148 of the soft-gel layer 144 is coupled to the second, patient-facing side 142 of the pressure-sensitive adhesive layer 138. The initial tackiness of the second, patient-facing side 150 of the soft-gel layer 144 is enough to initially couple the soft-gel layer 144 to the epidermis 116. Once in the desired location, a force is applied to the first side 134 of the liquid-impermeable-vapor permeable layer 132 of the releasable medical drape 106. For example, the user may rub the first side 134 of the liquid-impermeable, vapor-permeable layer 132 of the releasable medical drape 106. This action causes at least a portion of the pressure-sensitive adhesive layer 138 to be forced into the plurality of apertures 146 and into contact with the epidermis 116 to form contact couplings 152. The contact couplings 152 provide secure, releasable mechanical fixation to the epidermis 116.

The average effective diameter of the plurality of apertures 146 for the soft-gel layer 144 may be varied as one control of the tackiness or adhesion strength of the releasable medical drape 106. In this regard, there is interplay between three main variables for each embodiment: the thickness 154, the average effective diameter of the plurality of apertures 146, and the tackiness of the pressure-sensitive adhesive layer 138. The more pressure-sensitive adhesive layer 138 that extends through the apertures 146, the stronger the bond of the contact coupling 152. The smaller the thickness 154 of the soft-gel layer 144, the more pressure-sensitive adhesive layer 138 generally extends through the apertures 146 and the greater the bond of the contact coupling 152. As an example of the interplay, if a very tacky pressure-sensitive adhesive layer 138 is used and the thickness 154 is small, the average effective diameter of the plurality of apertures 146 may be relatively smaller. In one illustrative, non-limiting embodiment, the thickness 154 may be approximately 200 microns, the pressure-sensitive adhesive layer 138 is approximately 30 microns with a tackiness of 2000 g/25 cm wide strip, and the average effective diameter is approximately about 6 mm.

With the pressure-sensitive adhesive layer 138 forming contact couplings 152 via the plurality of apertures 146, vapor may be transmitted through the liquid-impermeable, vapor-permeable layer 132. Without the pressure-sensitive adhesive layer 138 touching the epidermis 116 or other aspects of the tissue site 102, humidity would have to bridge the gap between the tissue site 102 and the pressure-sensitive adhesive layer 138.

Figure 4:
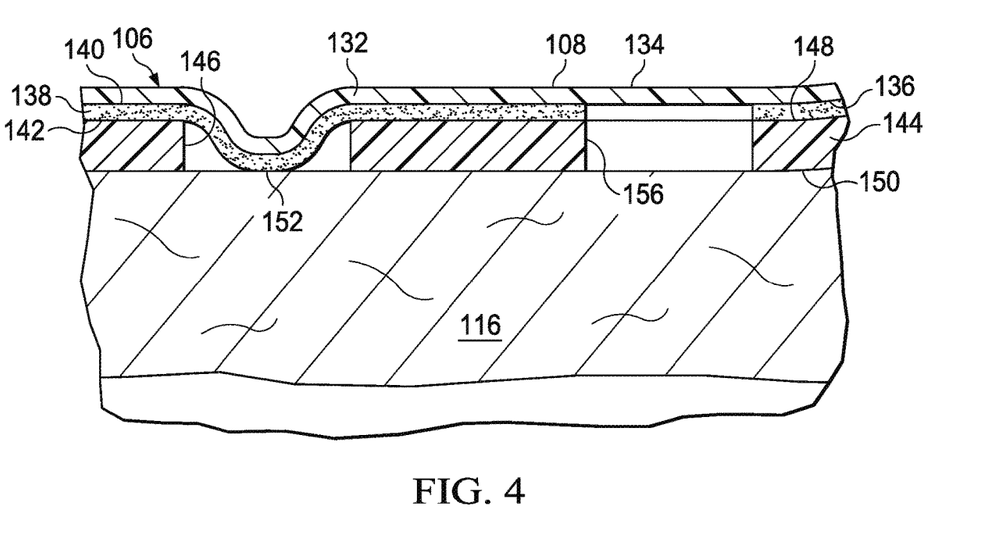
FIG. 4 is a cross-sectional view of a portion of another illustrative embodiment of a releasable medical drape shown adjacent to a tissue site.

A plurality of secondary apertures 156 (FIG. 4) may also be formed in the soft-gel layer 144 and pressure-sensitive adhesive layer 138. The secondary apertures 156 do not have any portion of the pressure-sensitive adhesive layer 138 extending into them during operation. The secondary apertures 156 may further facilitate vapor transfer through the liquid-impermeable, vapor-permeable layer 132.

Figure 5:
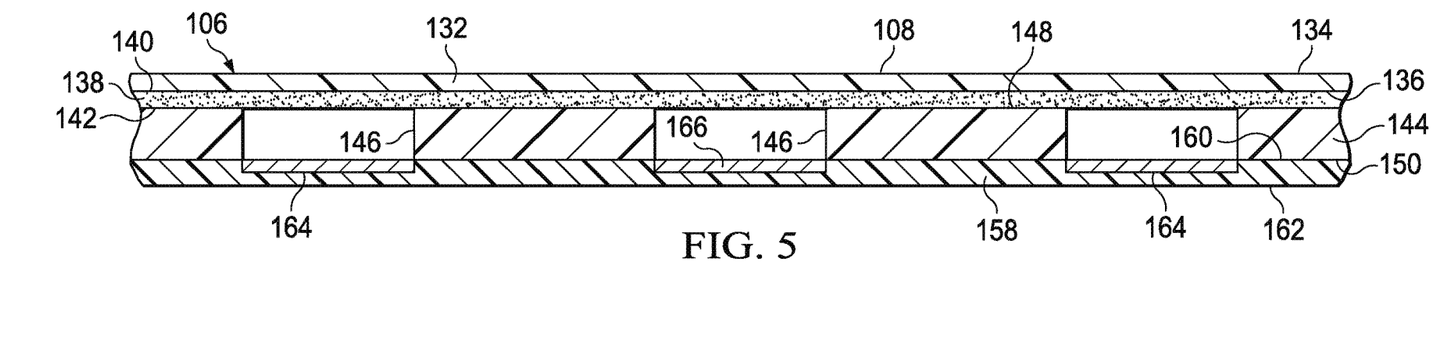
FIG. 5 is a cross-sectional view of a portion of another illustrative embodiment of a releasable medical drape.

A number of release members may be used in manufacturing, transporting, or use of the releasable medical drape 106. Referring now primarily to FIG. 5, a portion of a releasable medical drape 106 is presented. The releasable medical drape 106 is analogous in most respects to the releasable medical drape 106 of FIGS. 1-3, and accordingly, some parts are labeled but not further described here. A first release liner 158 having a first side 160 and a second side 162 covers the second, patient-facing side 150 of the soft-gel layer 144 prior to use. The first release liner 158 may be formed from high density polyethylene or any material that facilitates easy release from the soft-gel layer 144. In addition, a plurality of adhesive-release islands 164 are dispersed on the first side 160 of the first release liner 158 and are registered with the plurality of apertures 146. Thus, if any of the pressure-sensitive adhesive layer 138 extends through the apertures 146, the pressure-sensitive adhesive layer 138 will contact the plurality of adhesive-release islands 164. When ready to apply the releasable medical drape 106, the user removes the first release liner 158 thereby exposing the second, patient-facing side 150 of the soft-gel layer 144 and potentially the pressure-sensitive adhesive layer 138 that may extend through the apertures 146.

Figure 6:
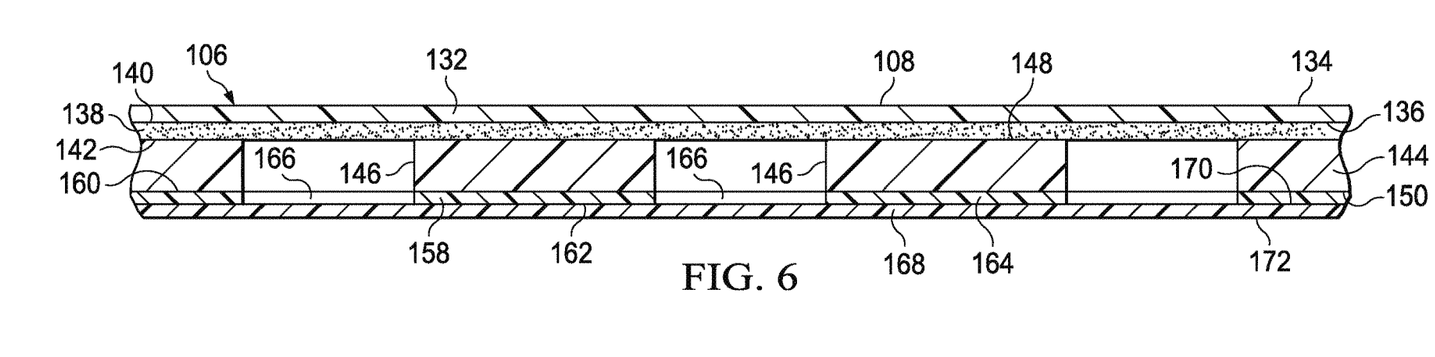
FIG. 6 is a cross-sectional view of a portion of another illustrative embodiment of a releasable medical drape.

Referring now primarily to FIG. 6, a portion of a releasable medical drape 106 is presented. The releasable medical drape 106 is analogous in most respects to the releasable medical drape 106 of FIGS. 1-3, and accordingly, some parts are labeled but not further described here. The first release liner 158 having the first side 160 and the second side 162 covers the second, patient-facing side 150 of the soft-gel layer 144 prior to use. The first release liner 158 may be formed from high density polyethylene or any material that facilitates easy release from the soft-gel layer 144. The first release liner 158 in this embodiment includes a plurality of apertures 166. The plurality of apertures 166 align, or register, with the plurality of apertures 146 in the soft-gel layer 144. In an illustrative embodiment, the plurality of apertures 166 and the plurality of apertures 146 in the soft-gel layer 144 are made at the same time. A second release liner 168 has a first side 170 and a second side 172. The first side 170 is applied to the second side 162 of the first release liner 158 so that the plurality of apertures 166 is covered by the second release liner 168. The second release liner 168 is formed from an adhesive-release material, e.g., polyolfin (polyethylene, polypropylene, cyclic olefin copolymer), polyester, polyamide, cellulosic (cellulose esters), and paper, optionally coated with a suitable release coating (silicone, fluoro copolymer [for example fluorosilicone], polyolefin wax.

In another illustrative embodiment, the soft-gel layer 144 is sufficiently thick and the first release liner 158 is sufficiently stiff that the pressure-sensitive adhesive layer 138 will not extend through the apertures 146. In this embodiment, only the first release liner 158 is used.

There are a number of ways that the releasable medical drape 106 may be manufactured. With reference to FIG. 6, according to one illustrative embodiment, the soft-gel layer 144 is cast onto the first side 160 of the first release liner 158. The plurality of apertures 146 and the plurality of apertures 166 are formed through the soft-gel layer 144 and first release liner 158 respectively. The apertures 146, 166 may be formed using shaped pins that puncture the materials as the materials move along a manufacturing path or by rolling a drum with shaped pins along the materials. The shaped pins are configured to make the desired shape and size of the apertures 146, 166. The second release liner 168 may then be applied to the second side 162 of the first release liner 158 to contact portions of the pressure-sensitive adhesive layer 138 extending through the apertures 146, 166. The liquid-impermeable, vapor-permeable layer 132 is applied to the first side 140 of the pressure-sensitive adhesive layer 138. In one embodiment, the pressure-sensitive adhesive layer 138 is presented as a transfer adhesive and brought into contact with the first side 140 of the pressure-sensitive adhesive 138 with laminating rollers. The releasable medical drape 106 is then fully assembled and is sterilized and packaged. The liquid-impermeable, vapor-permeable layer 132 may also be coated with pressure-sensitive adhesive layer 138 which is either dissolved in a solvent or dispersed in a continuous phase, which may be water, and the wet coating is dried.

Referring primarily to FIGS. 1-3, in operation according to one illustrative embodiment of the releasable medical drape 106 in the context of the system 100, the manifold 122 is disposed proximate to the tissue site 102. The releasable medical drape 106 is then applied over the manifold 122 and the tissue site 102 to form the sealed space 124. In applying, the releasable medical drape 106, any release liners (for example, the first release liner 158 or the second release liner 168) are removed and the second, patient-facing side 138 of the soft-gel layer 144 is applied to the intact skin 112 and over the manifold 122. The tackiness of the soft-gel layer 144 will hold the releasable medical drape 106 initially in position. The tackiness is such that if an adjustment is desired, the releasable medical drape 106 at this point may be removed and reapplied. Once the desired position is obtained for the releasable medical drape 106, the user uses hand pressure on the first side 134 of the liquid-impermeable, vapor-permeable layer 132. The hand pressure causes at least some portion of the pressure-sensitive adhesive layer 138 to extend through the plurality of apertures 146 and into contact with the epidermis 116 to form the contact coupling 152. Each contact coupling 152 is a firm—although releasable—attachment.

In another illustrative embodiment, the releasable medical drape 106 may include apertures and other means for allowing a release agent to contact the pressure-sensitive adhesive layer 138. The release agent diminishes the tackiness or adhesive strength of the pressure-sensitive adhesive layer 138 to thereby ease removal from the tissue site 102.

In another alternative embodiment, the soft-gel layer 144 is not a solid soft-gel layer, but a hydrophobic-coated material. For example, the soft-gel layer 144 may be formed by coating a spaced material (for example, woven, nonwoven, molded or extruded mesh) with a hydrophobic material (for example, a soft silicone). The hydrophobic-coated material is then laminated to the liquid-impermeable, vapor-permeable layer 132, for example, a polyurethane film. With this approach, apertures do not have to be formed as the pressure-sensitive adhesive layer 138 may extend through the opening in the spaced material. See FIGS. 7-10 as described below.

A prominent use of the releasable medical drapes 106 described herein is to create the sealed space 124 for reduced pressure therapy. Yet, the drape 106 may be used for other purposes. For example, the drape 106 may be used to releasably attach a strapless brazier to a person, to adhere a bandage to a patient, or any other purpose for which a releasable attachment to a person or animal is desired.

According to one illustrative embodiment, a releasable medical drape includes at least a liquid-impermeable, vapor-permeable layer, a pressure-sensitive adhesive layer, and a soft-gel layer having a plurality of apertures. The soft-gel layer is disposed next to the patient's skin. A portion of the pressure-sensitive adhesive layer extends through the plurality of apertures to contact the patient's skin. The soft-gel layer forms a good seal with the skin and the pressure-sensitive adhesive layer extending through the plurality of apertures forms a firm—but releasable—coupling with the patient's skin.

Figure 7:
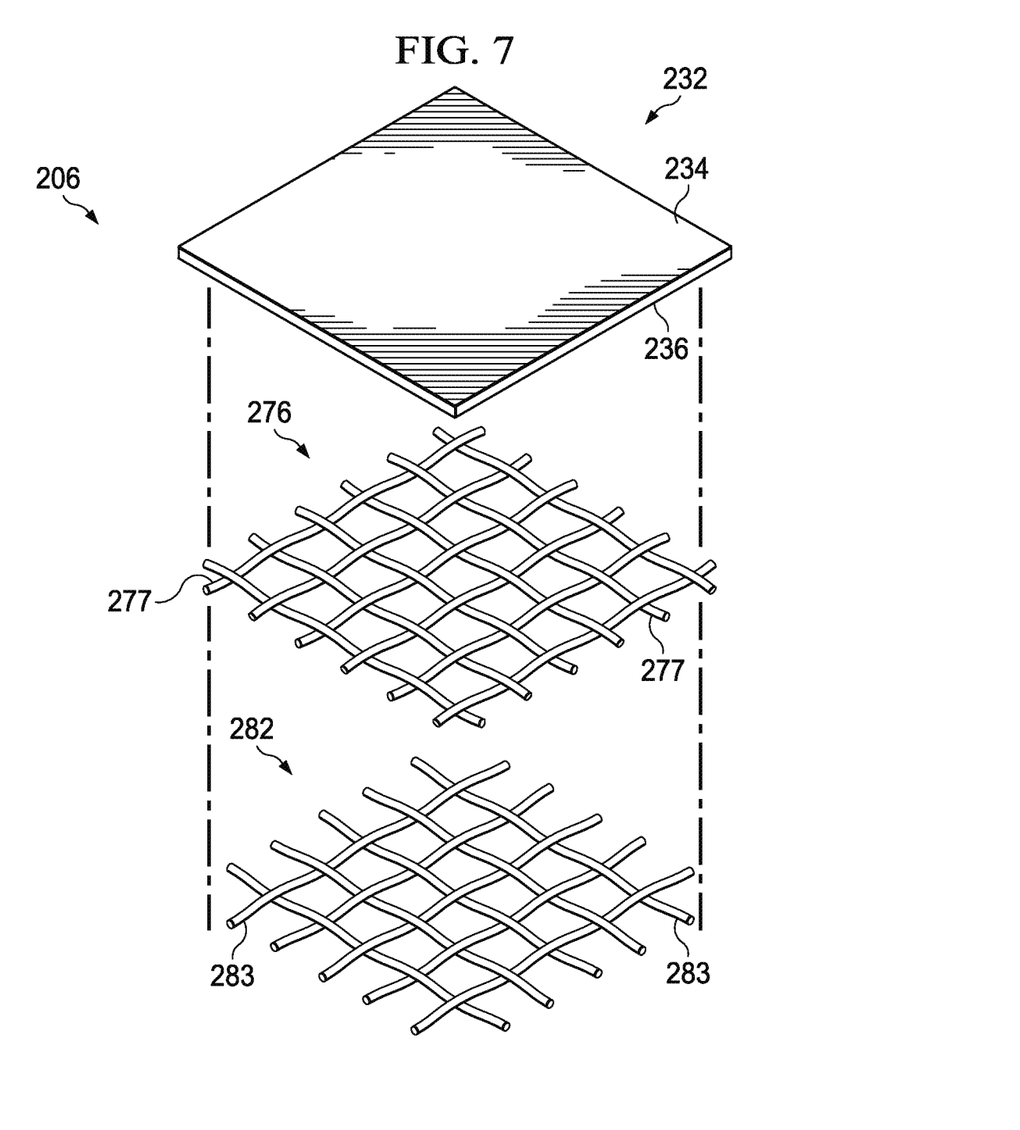
FIG. 7 is an exploded perspective view of another illustrative embodiment of a releasable medical drape.
Figure 8:
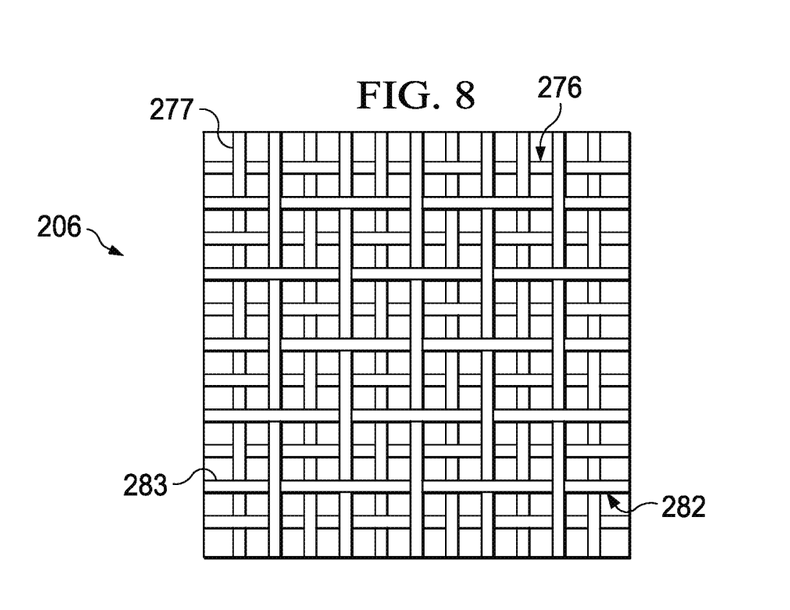
FIG. 8 is a plan view (from the second, patient-facing side) of the releasable medical drape of FIG. 7.

Referring now primarily to FIGS. 7-8, an illustrative embodiment of a releasable medical drape 206 is presented. The releasable medical drape 206 is analogous in many respects to the releasable medical drape 106 of FIGS. 1-6, and accordingly, some parts are labeled but not further described here.

The releasable medical drape 206 includes a liquid-impermeable, vapor-permeable layer 232 having a first side 234 and a second, patient-facing side 236. The releasable medical drape 206 has a first mesh layer 276 having a first side and a second, patient-facing side. The first mesh layer 276 comprises a first plurality of strands 277 that are interlocked. The first side of the first mesh layer 276 is coupled to the second, patient-facing side 236 of the liquid-impermeable, vapor-permeable layer 232. In this regard, the first side of the first mesh layer 276 may be laminated on to the second, patient-facing side 236 of the liquid-impermeable, vapor-permeable layer 232. Other coupling techniques may be used. At least the second, patient-facing side of the first mesh layer 276 is substantially coated with a pressure-sensitive adhesive.

The releasable medical drape 206 further includes a second mesh layer 282 having a first side and a second, patient-facing side. The second mesh layer 282 comprises a second plurality of strands 283 that are interlocked. The first side of the second mesh layer 282 is coupled to the second, patient-facing side of the first mesh layer 276 or to the second, patient-facing side 236 of the liquid-impermeable, vapor-permeable layer 232. The coupling of the second mesh layer 282 may be lamination or another coupling technique. At least the second, patient-facing side of the second mesh layer 282 is substantially coated with a soft-gel. As shown best in FIG. 8, the first mesh layer 276 and second mesh layer 282 are mis-registered so the plurality of strands 277, 283 have substantial portions that do not overlap. The pressure-sensitive adhesive of the first mesh layer 276 is configured to extend at least partially through void portions of the second mesh layer 282 when hand pressure is applied to the first side 234 of the liquid-impermeable, vapor-permeable layer 232.

Figure 9:
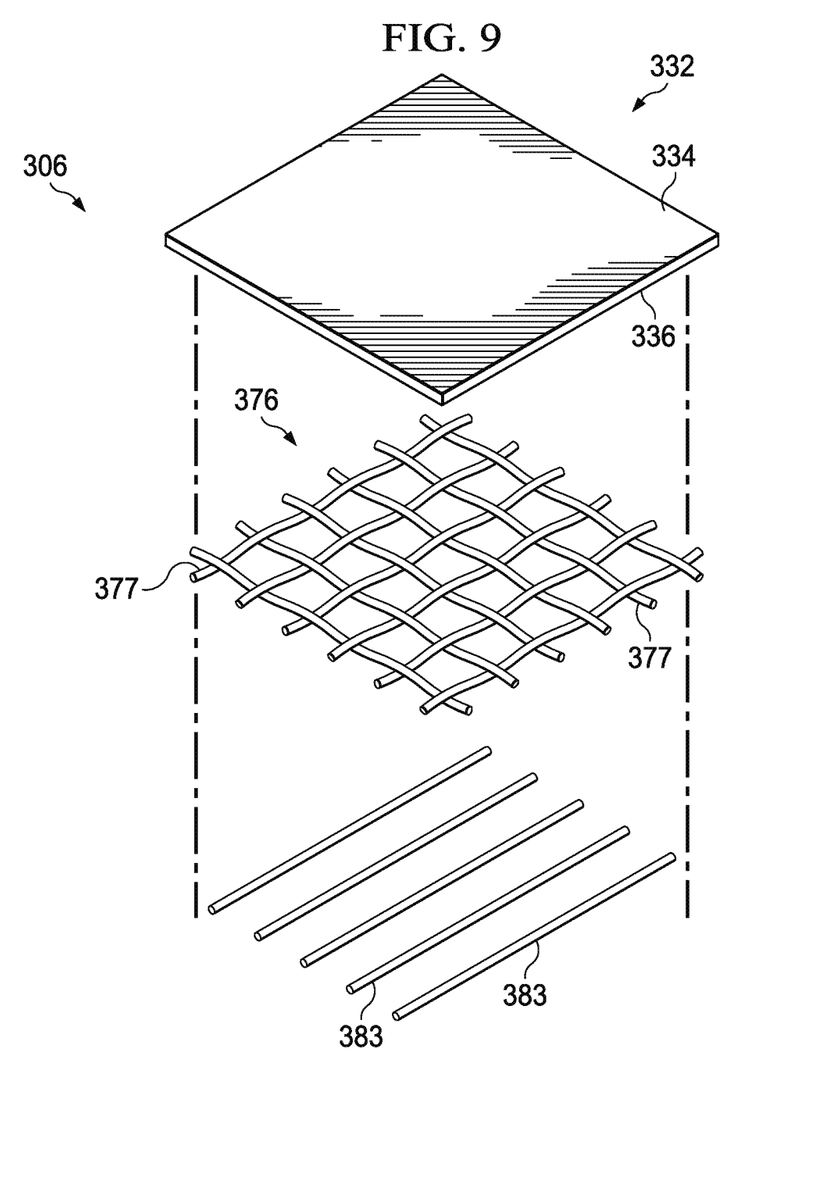
FIG. 9 is a exploded perspective view of an illustrative embodiment of a releasable medical drape.
Figure 10:
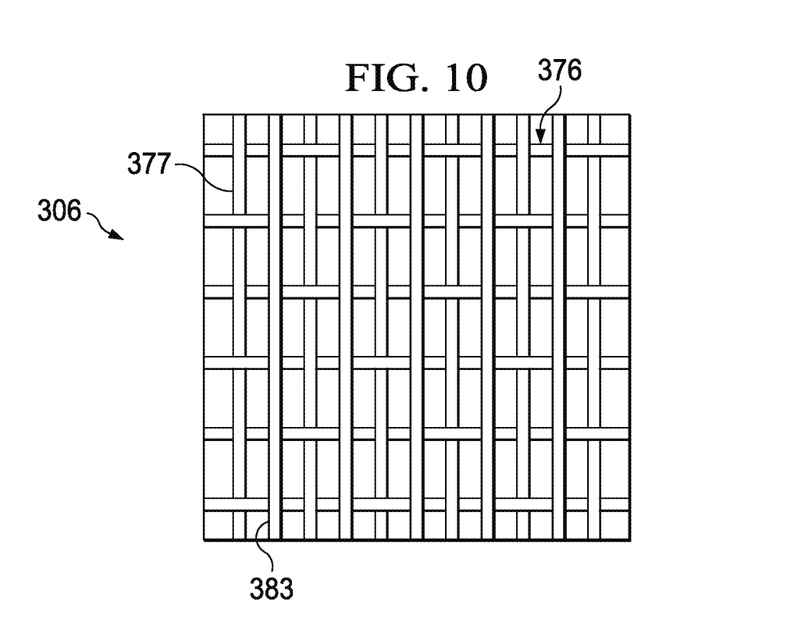
FIG. 10 is a plan view (from the second, patient-facing side) of the releasable medical drape of FIG. 9.

Referring primarily now to FIGS. 9-10, another illustrative embodiment of a releasable medical drape 306 is presented. The releasable medical drape 306 is analogous in many respects to the releasable medical drape 206 of FIGS. 7-8, and accordingly, some parts are labeled but not further described here. The primary difference between the releasable medical drape 306 and the releasable medical drape 206 is that the strands 377 and 383 may not form mesh layers, but may only be individual strands, i.e., not interlocked. For example, as shown in the figures, the first plurality of strands 377 may form a mesh layer, such as the first mesh layer 376 and the second plurality of strands 383 may form a loose layer, such as the second layer 382. Alternatively, the second plurality of strands 383 may form a mesh layer, but the first plurality of strands 377 may not. Alternatively, the first plurality of strands 377 and the second plurality of strands 383 may both form loose layers.

In one embodiment, the first plurality of strands 377 are substantially coated with a pressure-sensitive adhesive. The first plurality of strands 377 are coupled to the second, patient-facing side 336 of a liquid-impermeable, vapor-permeable layer 332. The second plurality of strands 383 is substantially coated with a soft-gel layer. The second plurality of strands 383 may be parallel to some of the first plurality of strands 377 or may take various patterns or be randomly placed. The second plurality of strands 383 is coupled at least in part to liquid-impermeable, vapor-permeable layer 332. The pressure-sensitive adhesive of the first plurality of strands 377 is configured to extend at least partially beyond the second plurality of strands 383 to contact the patient when hand pressure is applied to a first side 334 of the liquid-impermeable, vapor-permeable layer 332.

With both the releasable medical drapes 206 and 306, apertures need not be formed since gaps or void spaces will exist between the plurality of strands 277, 283, 377, 383. These approaches expose more of the liquid-impermeable, vapor-permeable layers directly to moisture and may thereby enhance vapor transmission. It should also be noted that in these embodiments, the order has been shown as liquid-impermeable, vapor-permeable layer, first plurality of stands, and then the second plurality of strands, but the first and second plurality of strands may be reversed in order.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection with any one embodiment may also be applicable to any other embodiment.

It will be understood that the benefits and advantages described above may relate to one embodiment or may relate to several embodiments. It will further be understood that reference to "an" item refers to one or more of those items.

The steps of the methods described herein may be carried out in any suitable order, or simultaneously where appropriate.

Where appropriate, aspects of any of the embodiments described above may be combined with aspects of any of the other embodiments described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A method of treating a tissue site, the method comprising:
    disposing a manifold proximate to the tissue site for distributing reduced pressure;
    covering the manifold and at least a portion of the tissue site with a releasable medical drape, wherein the releasable medical drape comprises:
        a liquid-impermeable, vapor-permeable layer having a first side and a second side,
        a pressure-sensitive adhesive layer having a first side and a second side, wherein the first side of the pressure-sensitive adhesive layer is coupled to the second side of the liquid-impermeable, vapor-permeable layer,
        a soft-gel layer having a plurality of apertures, a first side, and a second side, wherein the first side of the soft-gel layer is coupled to the second side of the pressure-sensitive adhesive layer, and
        wherein the pressure-sensitive adhesive layer is configured to extend at least partially through the plurality of apertures in the soft-gel layer in response to a force applied to the first side of the liquid-impermeable, vapor-permeable layer;
    applying a force to the first side of the liquid-impermeable, vapor-permeable layer to cause at least a portion of the pressure-sensitive adhesive layer to extend into the plurality of apertures and into contact with the tissue site; and
    delivering reduced pressure to the manifold.

2. The method of claim 1, wherein:
    the soft-gel layer comprises silicone;
    the pressure-sensitive adhesive layer comprises an acrylic adhesive; and
    the liquid-impermeable, vapor-permeable layer comprises a polyurethane film having a moisture vapor transfer rate greater than or equal to 300 g/m$^2$/24 hrs.

3. The method of claim 1, wherein the first side of the pressure-sensitive adhesive layer is coupled to the second side of the liquid-impermeable, vapor-permeable layer and the first side of the soft-gel layer is coupled to the second side of the pressure-sensitive adhesive layer.

4. A method of manufacturing a releasable medical drape, the method comprising:
    providing a soft-gel layer having a first side and a second side;
    forming a plurality of apertures in the soft-gel layer;
    providing a liquid-impermeable, vapor-permeable layer having a first side and a second side;
    providing a pressure-sensitive adhesive layer having a first side and a second side;
    coupling the first side of the pressure-sensitive adhesive layer to the second side of the liquid-impermeable, vapor-permeable layer so that the pressure-sensitive adhesive layer and the liquid-impermeable, vapor permeable layer are coterminous;
    coupling the second side of the pressure-sensitive adhesive layer to the first side of the soft-gel layer so that the pressure-sensitive adhesive layer and the soft-gel layer are coterminous;
    providing a first release liner having a first side and a second side;
    coupling the soft-gel layer to the first side of the first release liner, wherein the step of forming a plurality of apertures in the soft-gel layer comprises forming a plurality of apertures in the first release liner; and
    disposing a second release liner adjacent to the second side of the first release liner to engage portions of the pressure-sensitive adhesive layer extending through the plurality of apertures formed in the soft-gel layer and the first release liner.

5. The method of claim 4, wherein the first release liner is a polyethylene release liner having a plurality of areas comprising an adhesive release, the method further comprising registering the plurality of areas with the plurality of apertures formed in the soft-gel layer.

6. A releasable medical drape for providing a seal over a tissue site on a patient, the releasable medical drape comprising:
    a liquid-impermeable, vapor-permeable layer having a first side and a second side;
    a first mesh layer having a first side and a second side, wherein the first side of the first mesh layer is coupled to the second side of the liquid-impermeable, vapor-permeable layer, and wherein at least the second side of the first mesh layer is substantially coated with a pressure-sensitive adhesive;
    a second mesh layer having a first side and a second side, wherein the first side of the second mesh layer is coupled to the second side of the first mesh layer, and wherein at least the second side of the second mesh layer is substantially coated with a soft-gel; and
    wherein the pressure-sensitive adhesive of the first mesh layer is configured to extend at least partially through portions of the second mesh layer when hand pressure is applied to the first side of the liquid-impermeable, vapor-permeable layer.

* * * * *